United States Patent [19]

Salmon et al.

[11] 4,411,990

[45] Oct. 25, 1983

[54] PRIMARY BIOASSAY OF HUMAN TUMOR STEM CELLS

[75] Inventors: Sydney E. Salmon, Tucson, Ariz.; Anne W. Hamburger, Potomac, Md.

[73] Assignee: University Patents, Inc., Norwalk, Conn.

[21] Appl. No.: 254,346

[22] Filed: Apr. 15, 1981

Related U.S. Application Data

[63] Continuation of Ser. No. 48,190, Jun. 13, 1979, abandoned, which is a continuation of Ser. No. 922,722, Jul. 7, 1978, abandoned.

[51] Int. Cl.$^3$ .................... C12Q 1/18; C12Q 1/00; C12O 1/29
[52] U.S. Cl. .............................. 435/32; 435/4; 435/29
[58] Field of Search ............... 435/4, 29, 32, 33, 240, 435/241

[56] References Cited

U.S. PATENT DOCUMENTS

| | | | |
|---|---|---|---|
| 3,407,120 | 10/1968 | Weiss et al. | 435/240 |
| 3,865,689 | 2/1975 | Goldenberg | 435/240 |
| 3,873,423 | 3/1975 | Munder et al. | 435/240 |
| 3,935,066 | 1/1976 | Apostolov | 435/240 |
| 3,935,067 | 1/1976 | Thnyer | 435/240 |
| 3,959,074 | 5/1976 | Miller et al. | 435/235 |
| 4,038,145 | 7/1977 | Devlin | 435/34 |
| 4,055,966 | 10/1977 | Torney et al. | 435/240 |

OTHER PUBLICATIONS

Hamburger et al., "Primary Bioassay for Human Myeloma Stem Cells", Blood, vol. 47, (1976), p. 995.
Salmon et al., "Primary Bioassay of Ovarian Carcinoma Stem Cells", AACR Abstracts, vol. 19, (1978), p. 231, Abstract No. 922.
JAMA, vol. 237, No. 25, (1977), p. 2700.
Hyung, Diss. Abst. Int B, (1973), vol. 33(10), No. 4984-B.
Trisler, Diss. Abst. Int B, (1974), vol. 34(10), No. 5259-B.
Goldblum et al., "Enhancing Factor for In Vitro Growth of Human Plasma Cells", Chem. Abst., vol. 81, (1974), p. 312, Abs. No. 24041n.
Hachiro et al., "In Vivo Growth of Plasma Cytoma", Chem. Abst., vol. 78, (1973), p. 227, Abs. No. 14601g.
Salmon et al., "Quantitation of Differential Sensitivity of Human-Tumor Stem Cells to Anticancer Drug", New Eng. J. Med., vol. 298, (1978), pp. 1321-1329.
Frei et al., "Predictive Tests for Cancer Chemotherapy", New Eng. J. Med., vol. 298, No. 24, (1978), pp. 1358-1359.
Hamburger et al., Primary Bioassay of Human Tumor Stem Cells", Science, vol. 197, No. 4302, (1977), pp. 461-463.
Hamburger et al., "Primary Bioassay of Human Myeloma Stem Cells", J. Chm. Invest., vol. 60, (1977), pp. 846-854.
Hamburger et al., "The Nature of Cells Generating Human Myeloma Colonies in Vitro", J. Cell Physiol., vol. 98, No. 2, (1979), pp. 371-376.
Jones et al., "Development of a Bioassay for Putative Human Lymphoma Stem Cells", Blood, vol. 53, No. 2, (1978), pp. 294-303.
Hamburger et al., "Direct Cloning of Human Ovarian Carcinoma Cells in Agar", Cancer Res., vol. 38, (1978), pp. 3438-3444.
Salmon et al., "Immunoproliferation and Cancer: A Common Macrophage-Derived Promotor Substance", Lance, (1978), pp. 1289-1290.

Primary Examiner—Thomas G. Wiseman
Attorney, Agent, or Firm—Jerome M. Teplitz; A. Sidney Alpert; David N. Koffsky

[57] ABSTRACT

A bioassay method for supporting human tumor stem cell colony growth is disclosed. The method is suitable for culture of a variety of neoplasms of differing histopathology. Tumor stem cell colonies arising from different types of cancer have differing growth characteristics and colony morphology. The present bioassay may be employed in clinical studies of the effects of anticancer drugs or irradiation on human tumor stem cells.

25 Claims, No Drawings

PRIMARY BIOASSAY OF HUMAN TUMOR STEM CELLS

The invention described herein was made in the course of work under a grant or award from the Department of Health, Education and Welfare.

This is a continuation of application Ser. No. 048,190 filed June 13, 1979, which is in turn a continuation in part of application Ser. No. 922,722, filed July 7, 1978, both now abandoned.

BACKGROUND OF THE INVENTION

The present invention relates to tissue culture systems and, more particularly, to a culture system capable of supporting human tumor stem cell colony growth in vitro.

Tumor stem cells are the cell renewal source of a neoplasm and also serve as the seeds of metastatic spread of cancer. Studies of transplantable tumors in animals indicate that tumor stem cell colony-forming assays, either in vivo or in vitro, can be used to study the biological properties of these cells and to delineate differences in individual sensitivity to a variety of chemotherapeutic agents, as described, for example, by M. Ogawa et al., *Blood* 41, 7 (1973) and by G. Steel et al., *Cancer Res.*, 35, 1530 (1975). As an example of such a study, the development of an in vitro colony-forming assay for stem cells from transplantable mouse myeloma (a plasma cell neoplasm) permitted detailed analysis of the effects of anticancer drugs in vitro, and the assays are predictive of therapeutic responses even in animals with advanced mouse myeloma. Such an analysis is described by C. Park et al., *J. Nat. Cancer Inst.*, 46, 411 (1971).

The ability to grow colonies from primary tumor cell explants in semisolid culture media has even greater potential application. Unfortunately, primary explantation of human tumors for colony formation in vitro has met with little success. One major problem has been the creation of an environment that gives tumor cells a selective advantage over normal cells. Several investigators have had occasional success in obtaining colony growth in soft agar with pediatric solid tumors, as described, for example, by R. McAllister et al., *Pediatr. Res.*, 2, 356 (1968) and A. Altman et al., *Cancer Res.*, 35, 1809 (1975). Most recently, the effect of drugs on human stem cell colonies has been studied with the use of xenografts established in nude mice and then culturing cells from these grafts in agar in diffusion chambers intrapertioneally implanted in mice that had been irradiated, as discussed by I. E. Smith et al., *Br. J. Cancer*, 34, 476 (1976). However, such multiple-step systems have not been clinically practical.

A standard colony-forming assay for human tumor stem cells could be used to determine the sensitivity of tumor cells from individual patients to drugs, irradiation, and other therapeutic modalities and would permit the demonstration of resistant clones of cells in previously treated patients. The development of such a colony-forming assay seems especially important in view of evidence described by P. Roper et al., *Cancer Res.*, 36, 2182 (1976) indicating that the only valid measure of drug efficacy in killing an established culture of human lymphoma cells is the inhibition of their colony-forming capability.

SUMMARY OF THE INVENTION

In accordance with the present invention, there has now been developed an in vitro assay which supports human tumor stem cell colony growth from primary explanted cells obtained from a wide variety of primary or metastatic human tumors, and appears to preclude growth of normal hematopoietic precursors. The assay empolys a two-layer semi-solid or solid culture system exhibiting interlayer diffusibility of dissolved nutrients and growth factors. The assay is carried out by first forming a cell-free gelled underlayer comprising a liquid tissue culture feeder nutrient medium capable of supporting human tumor cell growth and a gelling agent for such feeder nutrient medium. A gelable liquid single-cell suspension of the explanted cells to be cultured is then prepared in a liquid tissue culture carrier nutrient medium capable of supporting human tumor cell growth and containing a gelling agent for such carrier nutrient medium. The suspension is then plated onto the underlayer and gelation thereof is allowed to occur, thereby forming a tumor cell-containing gelled overlayer which together with the underlayer constitutes the two-layer culture system. The culture system further contains, as an essential ingredient, a tumor stem cell colony growthpromoting concentration of a macrophage-elaborated tumor growth factor, which we have denominated METGF, described more fully hereinafter. The required concentration of METGF is dissolved within at least one of the two layers. The culture system is then incubated for a period of time sufficient to grow tumor stem cell colonies.

Within certain concentration ranges of the explanted cells in the suspension, a substantially proportional or linear relationship has been found to exist between the total number of explanted cells present in the overlayer and the total number of resulting tumor stem cell colonies grown during the incubation period. This latter number represents the total number of viable colony-forming tumor cells present in the overlayer, and thus enables a quantitative assay of the overlayer for its viable colony-forming tumor stem cell content. Such quantitative assay forms the basis for quantitatively measuring the sensitivity of the tumor stem cells to exposure to various dose levels of various known or potential anticancer drugs, thereby providing an indication of the antineoplastic activity of such drugs against the specific human tumor from which the explanted cells were obtained. Preliminary evidence indicates that the present assay system has highly promising utility for the in vitro prediction of clinical response to cancer chemotherapy, as well as in the screening of new anticancer drugs for clinical trial.

DESCRIPTION OF PREFERRED EMBODIMENTS

The assay of the present invention has universality of application in that it supports human tumor stem cell colony growth from primary explanted cells obtained from substantially all known primary or metastatic human tumors, including solid tumors (both carcinomas and sarcomas) as well as hematological cancers (lymphomas and myelomas). The various types of carcinomas (adeno, squamous and undifferentiated varients for carcinomas of various sites), to which the present assay are applicable include, for example, adrenal, bladder, breast, colon, kidney, lung, ovary, pancreas, prostate, thyroid, upper airways (head and neck), uterus (corpus and cervix), bile ducts, choriocarcinoma, esophagus, liver, parathyroid, rectum, salivary glands, small bowel, stomach, testis, tongue and urethra. The various types of sarcomas and other neoplasms to which the present assay are applicable include, for example, chronic lymphocytic leukemia, diffuse lymphomas, Ewing's tumor, Hodgkin's disease, macroglobulinemia, melanoma (melanotic and amelanotic), multiple myeloma, nephroblastoma (Wilm's tumor), neuroblastoma, nodular lymphomas, rhabdomyosarcoma, angiosarcoma, brain tumors (gliomas), chondrosarcoma, dysgerminoma, fibrosarcoma, leiomyosarcoma, liposarcoma, meduloblastoma, mesothelioma, osteosarcoma, retinoblastoma and thymoma.

Various liquid tissue culture nutrient media capable of supporting human tumor cell growth are known in the art and can suitably be empolyed as either the feeder nutrient medium or the carrier nutrient medium. A nutrient medium found to be particularly suitable for use as the feeder nutrient medium is RPMI 1640 medium enriched with 15% heat-inactivated fetal calf serum. RPMI 1640 medium is a liquid tissue culture medium developed at Roswell Park Memorial Institute and designed specifically for cultivating human and mouse leukemia cells in tissue culture (Iwakata et al., New York Journal of Medicine, 64/18:2279–2282, Sept. 15, 1964; and Moore et al., J. Nat. Can. Inst., 36/3:405, March, 1966). The composition of RPMI 1640 medium is set forth in U.S. Pat. No. 4,038,145, issued July 26, 1977, and is incorporated herein by reference. A nutrient medium found to be particularly suitable as the carrier nutrient medium is CMRL 1066 medium (Grand Island Boilogical Co.) supplemented with 20 percent horse serum, penicillin (100 unit/ml), streptomycin (2 mg/ml), glutamine (2 mM), $CaCl_2$(4 mM), insulin (3 unit/ml), asparagine (0.1 mg/ml), and DEAE dextran (0.5 mg/ml). While the two nutrient media described above for the feeder nutrient medium and the carrier nutrient medium, respectively, are the preferred nutrient media to be employed in the system, it will be understood that other similar nutrient media can be suitably substituted therefor.

The preferred gelling agent for use with both the feeder nutrient medium in the underlayer and the carrier nutrient medium in the overlayer is agar since it exhibits the desirable combination of properties of water retention, a firm growing surface when cool, ease of handling when dissolved in boiling water, and allowed mobility of the nutrient ions. However, various other gelling agents commonly empolyed in cell and tissue culture systems, such as, for example, silica gel, are also suitable. Due to the presence of the gelling agent, each of the two layers of the system are in semi-solid or solid condition, with the underlayer serving not only the function of supplying the cells in culture with the requisite nutrients and growth factors, but also the function of maintaining the cells separated from the surface of the culture dish.

An essential ingredient of the culture system for successfully carrying out the assay of the present invention is a tumor stem cell colony growth-promoting concentration of METGF. METGF is a water-soluble tumor growth factor which is elaborated by macrophages. While METGF has not as yet been isolated for chemical identification and characterization, immunological studies have established that it is not antigenically related to the colony-stimulating factor (CSF) needed for normal granulocyte colony formation and described by Metcalf, Hematopoietic Colonies, Springer Verlag, Berlin (1977). It has furthermore been established that METGF is not the same as the phagocytic cell factor described by Namba et al., J. Immunol., 109, 1193 (1972).

Whatever may be its chemical identity or its mechanism of action, METGF has been found to effectively promote tumor stem cell colony growth when dissolved within the culture system, in either or both of the two layers thereof, in a definable concentration range. Such concentration range is, broadly, from about 1.5 to about 15 units per milliliter of the culture system and, preferably, from about 6.25 to about 12.5 units per milliliter of the culture system, wherein one unit of METGF is defined as the tumor growth-promoting activity in 10 microliters of a "standard conditioned medium".

The "standard conditioned medium" used as the METGF reference standard is RPMI 1640 medium enriched with 15% heat-inactivated fetal calf serum and conditioned by the adherent spleen cells of BALB/c mice that had been primed with 0.2 ml of mineral oil injected intraperitoneally four weeks previously. The adherent cells are obtained as follows: The spleens are teased with needles to form a single-cell suspension, and $5 \times 10^6$ cells are placed in a 60-mm Falcon petri dish for two hours to permit the cells to adhere. The dishes are then washed three times in cold phosphate-buffered saline. The cells are incubated for three days at 37° C. in RPMI 1640 medium enriched with 15% heat-inactivated fetal calf serum, following the method of Namba et al., supra. The conditioned medium is then decanted and centrifuged at 400 g for 15 minutes, and the supernatant is then passed through a 0.45 $\mu$m Nalgene filter and stored at $-20°$ C.

The tumor stem cell colony growth-promoting concentration of METGF may be incorporated into the culture system either by way of the underlayer or by way of the overlayer or a combination of the two. Preferably, at least a portion of the METGF concentration present in the culture system originates from the underlayer by employing as the feeder nutrient medium a macrophage-conditioned nutrient medium containing METGF dissolved therein. For example, the feeder nutrient medium may be a nutrient medium which has been macrophage-conditioned by incubation either with the adherent spleen cells of mineral oil-primed BALB/c mice (i.e., the "standard conditioned medium" described above) or with the cells from a human B lymphocyte cell line. In either case, the macrophage-conditioned nutrient medium should be rendered cell-free prior to formation of the underlayer, since the presence of the cells in the underlayer interferes with the human tumor stem cell colony growth. Furthermore, at least a portion of the METGF concentration present in the culture system may originate from the overlayer. This comes about as a result of the explanted cells which are placed in the overlayer-forming suspension including autologous macrophages which, in turn, elaborate METGF. Regardless of which layer the METGF originates from, its total concentration within the system should be within the range indicated above.

The underlayer portion of the culture system may suitably be formed by first preparing a gelable liquid solution containing the feeder nutrient medium and the gelling agent. If the METGF is to be furnished from the underlayer, such gelable liquid solution should contain the requisite concentration of METGF. A suitable gelable liquid solution would be, for example, a 25% by volume solution of the "standard conditioned medium" described above in 0.5% Bacto agar. By the definition of one unit of METGF set forth above, the METGF concentration of such gelable liquid solution would be 25 units per milliliter. Thus, if the underlayer and the overlayer are employed in equal volumes in preparing the culture system, the METGF concentration in the culture system will be 12.5 units per milliliter, which is within the requisite range of METGF concentration.

After preparing the gelable liquid solution of the feeder nutrient medium and the gelling agent therefor, such solution is plated onto the surface of the culture dish and allowed to gel, thereby forming the underlayer portion of the culture system.

The explanted cells to be cultured are obtained by biopsy from primary or metastatic human tumors employing a aseptic cell collection techniques well known in the art. The explanted cells are preferably first subjected to a fractionation treatment so as to effect removal therefrom of contaminating non-tumor cells. Suitable fractionation techniques are well known in the art and include, for example, velocity gradient sedimentation (as described by Miller et al., *J. Cell Physiology*, 73, 191–201 [1969],incorporated herein by reference) and adherent cell depletion (as described by Messner et al., *Blood*, 42, 701–710 [1973], incorporated herein by reference). Preferably, a combination of the velocity gradient sedimentation and adherent cell depletion techniques is employed.

A gelable liquid single-cell suspension is then prepared of the explanted cells in the carrier nutrient medium containing a gelling agent therefor. For example, the explanted cells may be suspended in a solution of the carrier nutrient medium in 0.3% Bacto agar. The concentration of the explanted cells in the suspension should be selected so as to be within a range enabling a substantially linear or proportional relationship to exist between the total number of the explanted cells which will be present in the overlayer portion of the culture system and the total number of resulting tumor stem cell colonies which will be grown during the culture. While the requisite cell concentration may vary somewhat depending upon the type of tumor cells being cultured, such substantially linear relationship will generally exist when the concentration of the explanted cells in the suspension is within the range of from about $1 \times 10^4$ to about $1 \times 10^6$ cells per milliliter.

Since thiols such as, for example, 2-mercaptoethanol or monothioglycerol, have been found in many cases to enhance tumor colony growth, a thiol will preferably be added to the gelable cell suspension in a concentration, for example, of from about $5-10 \times 5$ M to about $5 \times 10^{-4}$ M.

The gelable suspension of explanted cells is then plated onto the underlayer, generally in a volume substantially equal to that of the underlayer, and gelation of the suspension is then allowed to occur, thereby forming the tumor cell-containing gelled overlayer which together with the underlayer constitutes the two-layer culture system. This culture system is then incubated under standard incubation conditions, for example, at a temperature of about 37° C. in a humidified atmosphere containing from about 5 to about 7.5% $CO_2$. The incubation is allowed to proceed without any further feeding for a period of time sufficient to grow tumor stem cell colonies, typically defined as collections of more than 40 cells, which colonies are readily observable by techniques well known in the art. While the requisite incubation period will vary somewhat depending upon the type of tumor cells being cultured, colony formation will generally be observed after an incubation period ranging from about 7 days to about 21 days.

Since each viable colony-forming tumor stem cell present in the culture system will propagate a separate tumor stem cell colony during the incubation period, the total number of resulting tumor cell colonies grown during the incubation period represents the viable colony-forming tumor stem cell content of the overlayer. Colony counting at the termination of the incubation period can be carried out by techniques well known in the art. Thus, by forming the overlayer from a determinate volume of the explanted cell suspension having a determinate concentration of the explanted cells, the culture system of the present invention enables a quantitative assay for the viable colony-forming tumor stem cell content of the explanted cell specimen. The most significant utility of such quantitative assay is in quantitatively measuring the sensitivity of the tumor stem cells to exposure to various dose levels of various known or potential anticancer drugs, thereby providing an indication of the antineoplastic activity of such drugs against the specific human tumor from which the explanted cells were obtained.

In carrying out such drug sensitivity measurements, the sensitivity of the tumor stem cells to exposure to one or more given dose levels of a given drug is measured by individually culturing aliquots of the same explanted cells utilizing a plurality of the two-layer culture systems of the present invention in combination. One of the aliquots serves as a control and is quantitatively assayed for the viable colony-forming tumor stem cell content thereof in the absence of drug exposure. Each of the other of the aliquots is exposed to the drug at a different of the dose levels and is then quantitatively assayed for the surviving drug-exposed colony-forming tumor stem cell content thereof. The percent reduction in the assay count resulting from the drug exposure may then be determined for each of the drug levels tested.

Drug exposure of the cells for the purposes of the drug sensitivity measurements is preferably carried out prior to preparing the gelable cell suspension used in forming the overlayer. The procedure involves incubating the explanted cell aliquot with a determinate concentration of the drug for a determinate period of time, and thereafter separating the aliquot from the drug and washing the aliquot free of residual drug. The washed drug-exposed aliquot will then be ready for use in preparing the gelable liquid suspension for forming the overlayer. Alternatively, the drug exposure may be carried out by incorporating a determinate concentration of the drug into the gelable liquid suspension and maintaining the drug in the overlayer throughout the determinate culture incubation period. Since the term "drug exposure dose level", as used herein, refers to the quantitative product of the drug concentration (e.g., in $\mu g/ml$) and the time of the exposure period (e.g., in hours), this latter alternative procedure will generally involve employing extremely low drug concentrations. In either case, it has been found that the drug exposure dose level required in carrying out the drug sensitivity measurements in accordance with the assay of the present invention, is at a maximum of only 5 to 10% of the clinically achievable drug exposure dose level for the known anticancer drugs which have been tested in the present system.

In the preferred technique of carrying out the drug exposure by incubation prior to forming the gelable explanted cell suspension, the drug exposure incubation is carried out at 37° C., typically for a period of one hour utilizing the appropriate drug concentration for achieving the desired drug exposure dose level.

The drug sensitivity measurements as described above can be carried out in a manner which enables the determination, for any given drug, of a "drug sensitivity index", which is indicative of the antineoplastic activity of the given drug against the specific human tumor from which the explanted cells were obtained. This procedure involves carrying out the drug sensitivity measurements for a plurality of dose levels extending over a multi-log range, and then using the results of these measurements to plot a curve of percent survival (the percentage of the assay count resulting from drug exposure versus the assay count of the control in the absence of drug exposure) versus drug exposure dose level. The "drug sensitivity index" of the given drug is then quantitated by measuring the area under such curve out to a defined upper limit which is correlated to the clinically achievable peak drug exposure dose level for that drug. Due to the exquisite sensitivity of the in vitro assay of the present invention, suitable cutoff drug exposure dose levels for determining a reliable sensitivity index have been found to be only 5 to 10 percent of the clinically achievable peak drug exposure dose levels for the known anticancer drugs which have been tested in the system. For example, for melphalan, the cutoff drug exposure dose level for a reliable sensitivity index would be a 1-hour exposure to a concentration of 0.1 $\mu g/ml$ of the drug, which is less than 10 percent of the achievable melphalan exposure dose level in vivo. A similar relationship has been found with many other known anticancer drugs.

The sensitivity index obtained in the above-described manner is highly indicative of the antineoplastic activity of the drug against the specific human tumor from which the explanted cells where obtained, with a low sensitivity index indicating high antineoplastic activity. In tests thus far carried out for correlating clinical data with the results achieved in the in vitro assay of the present invention, it has been found that an in vitro sensitivity index of less than 3 corresponds to high antineoplastic activity in vivo, an in vitro sensitivity index of from 3 to 5.3 corresponds to intermediate antineoplastic activity in vivo, and an in vitro sensitivity index of greater than 5.3 corresponds to substantially no antineoplastic activity in vivo.

Preliminary evidence indicates that the in vitro assay system of the present invention has highly promising utility for the in vitro prediction of clinical response to cancer chemotherapy, as well as in the screening of new anticancer drugs for clincal trial. For example, in treating a specific patient for a specific tumor, the explanted cells obtained from a biopsy of such specific tumor can be assayed in accordance with the present technique, and drug sensitivity measurements can be carried out for a plurality of different anticancer drugs which are potentially clinically effective for the chemotherapeutic treatment of the specific tumor. After determining the relative drug sensitivity indices for each of the various drugs tested, these sensitivity indices may be used for predictably selecting the most promisingly effective of the drugs to be used for the chemotherapeutic treatment. In preliminary clinical trials of this technique, both retrospective and prospective, the correlation found between the in vitro prediction and the in vivo response was impressively high, approaching 100%.

The invention is further illustrated by way of the following examples detailing the procedures employed in carrying out the in vitro assay of the present invention with several types of human tumors.

EXAMPLE 1

Bone marrow cells were collected aseptically, in preservative-free heparin, from consenting normal volunteers and patients with various neoplasms with known bone marrow involvement. Malignant ascites was collected (in heparin) by paracentesis. Red blood cells were removed from the bone marrow samples by sedimentation in 3.0 percent dextransaline, and the supernatant bone marrow cells were collected and then washed three times in Hanks balanced salt solution with 10 percent fetal calf serum that had been inactivated by heat. The number of viable cells was determined by hemocytometer counts with trypan blue.

Cells to be tested were suspended in an agar-containing nutrient medium such as, for example, 0.3 percent Bacto agar (Difco) in CMRL 1066 supplemented with 20 percent horse serum, penicillin (100 unit/ml), streptomycin (2 mg/ml), glutamine (2 mM), $CaCl_2$ (4 mM), insulin (3 unit/ml), asparagine (0.1 mg/ml), and DEAE dextran (0.5 mg/ml) to yield a final concentration of $5 \times 10^5$ cell/ml. 2-Mercaptoethanol was added at a concentration of $5 \times 10^{-5}$ M immediately before the cells were plated. A portion (1 ml) of the resultant cell suspension was pipetted onto a 1.0-ml cell-free gelled underlayer which combined 0.2 ml of "standard conditioned medium" (as described above) in 0.5 percent Bacto agar, in 35-mm plastic petri dishes, and gelation of the cell suspension was allowed to occur. Cultures were incubated under conditions such as a temperature of 37° C. in 5 percent $CO_2$ in a humidified atmosphere for approximately 3 weeks with no additional feeding.

With respect to myeloma, clusters of 8 to 40 cells appeared 5 to 10 days after plating, whereas colonies, defined as collections of more than 40 cells, appeared 14 to 21 days after plating. Colonies consisted of 40 to several hundred large ($>20$ $\mu m$) round cells. Cells in myeloma colonies appeared to pile up on one another, as compared to cells in rare contaminating granulocyte colonies in which cells were loosely aggregated. The number of granulocyte colonies in different cultures varied, but never exceeded 10 percent of the total number of colonies. Since granulocyte colony growth occurred more frequently when $10^6$ nucleated cells were plated in a culture dish, a standard concentration of $5 \times 10^5$ marrow cells per dish was chosen to minimize stimulation of granulocyte colony formation. In general, the concentration may range from about $1 \times 10^5$ to about $1 \times 10^6$ cells per dish.

Colony growth of normal human granulocyte macrophage progenitors has been to be dependent on the presence of a specific humoral stimulus, colony stimulating factor (CSF), as discussed by T. Bradley et al., *Aust. J. Exp. Biol. Med. Sci.*, 4, 287 (1966). Although no exogenous source of CSF is supplied in the present culture system, adherent bone marrow cells can elaborate endogenous CSF. Depletion of these CSF-producing cells, before plating, by allowing adherence to plastic or uptake of carbonyl iron, did not reduce the number or size of myeloma colonies. In addition, antibody to CSF did not appear to reduce the number of myeloma colonies. Thus, it is concluded that colony growth in the present system is not dependent on CSF and that the contamination of myeloma colonies by granulocyte colonies is minimal.

The number of myeloma colonies was 5 to 500 per plate, yielding a plating efficiency of 0.001 to 0.1 percent, which compared favorably with analogous systems. The number of myeloma colonies was proportional to the number of cells plated between concentrations of $10^5$ to $10^6$ cells per plate, and the plot could be extrapolated back to zero, suggesting colony origin from a single monoclonal plasma cell. In order to enrich the myeloma stem cell fraction and obtain higher plating efficiencies, there was applied a combination of velocity gradient sedimentation (Ig) and adherent depletion of nonmyeloma cells. The velocity gradient sedimentation may be carried out by the method as described by R. Miller et al., *J. Cell Physiology*, 73, 191–201 (1969), incorporated herein by reference. Adherent depletion may be carried out by the method as described by H. Messner et al., *Blood*, 42, 701–710 (1973), incorporated herein by reference. In initial experiments a 20-fold increase in plating efficiency was obtained with the combination of these techniques.

Cells from individual colonies plucked from the agar with a pipette appeared to be plasma cells when examined by light microcopy after staining with Wright-Giemsa and methyl green pyronine. They were peroxidase negative, incapable of phagocytosis of neutral red or latex particles, and positive for plasma cell acid phosphatase. Immunofluorescence studies demonstrated that 60 to 80 percent of the myeloma plasma cells contained intracytoplasmic monoclonal immunoglobulin of immunologic specificity, qualitatively identical to the type present in the serum or urine of the patient studied. Colony growth has been obtained in more than 86 percent of the total myeloma cases and in more than 89 percent of previously untreated myeloma patients (Table 1). In contrast, when a series of bone marrow samples from ten normal volunteers was tested in the same culture system, only a rare granulocyte colony would form and undergo deterioration within 10 days (Table 1). The system was not optimized for granulocyte colony formation.

It was also found that the same conditioned medium underlayer supported tumor colony growth by a variety of metastatic cancers. Table 1 summarizes this experience. In addition to myeloma and the related disorder, Waldenstrom's macroglobulinemia, tumor colony growth occurred from bone marrows of patients with disseminated lymphoma, neuroblastoma and oat cell carcinoma of the lung. Tumor colony growth was also obtained from malignant ascites from patients with ovarian adenocarcinomas (Table 1). Histological studies indicated that the colonies were derived from the tumor of origin.

TABLE 1

Growth of Tumor Stem Cell Colonies From Various Human Neoplasms

| Type of tumor (source of sample)[a] | Subjects with positive cultures per total subjects tested[b] | Colonies per $5 \times 10^5$ cells plated in positive cultures | Required incubation time (days) |
|---|---|---|---|
| Normal volunteers (controls) (M) | 2/10[c] | 1–4[c] | 7 |
| Multiple myeloma (M) | 56/63 | 5–500 | 21 |
| Non-Hodgkin's lymphoma (M) | 9/18 | 41–150 | 14 |
| Hodgkin's disease (M) | 0/3 | | |
| Waldenstrom's macroglobulinemia (M) | 3/3 | 50–150 | 21 |
| Chronic lymphocytic leukemia (M) (N) | 2/9 | 20–200 | 21 |
| Oat cell carcinoma of the lung (M) | 1/1 | 100 | 14 |
| Adenocarcinoma of the ovary (A) | 8/8 | 100–800 | 12 |
| Melanoma (N) | 2/3 | 80–150 | 21 |
| Neuroblastoma (M) | 1/1 | 250 | 7 |

Notes:
[a] (M), bone marrow aspirate; (N), lymph node; (A), malignant ascites collected by paracentesis
[b] In some of the tumor categories, failure to obtain colony growth from a particular sample may be due to prior cytotoxic chemotherapy or specific histological subtype (such as in the non-Hodgkin's lymphomas) where there may be differences in growth requirements.
[c] Granulocyte-macrophage colonies.

Colony morphology, colony growth kinetics and plating efficiency varied with the different tumors tested, but these criteria were constant for each individual tumor type (Table 1). Colonies from bone marrows of patients with lymphoma appeared 4 days after plating, reached a peak size 7 days after plating and degenerated after 3 weeks in culture. Individual cells were smaller than those of myeloma stem cell colonies (approximately 10 μm), but the number of cells per colony reached several thousand—an amount greater than seen in myeloma colonies. Tumor colonies from the bone marrow of a patient with neuroblastoma grew as a sphere of large (>25 μm), round, tightly packed cells. These colonies grew rapidly and continued to grow for 5 weeks. Ovarian adenocarcinoma cells retained their epithelial morphology, and the plating efficiency of these was high enough to indicate linear increase in colonies with increasing numbers of cells plated above $10^3$ cells. The characteristic morphology and individual growth kinetics of each colony type have allowed a distinction to be drawn between stem cells colonies of different tumor types and between tumor stem cell colonies and the occasional colonies of normal granulocyte-macrophage precursors.

It is believed that application of such simple in vitro culture techniques for studies of human tumor stem cells from primary explants will prove of clinical importance. First, the technique permits characterization of many of the biophysical properties of tumor stem cells, such as sedimentation velocity, fraction in the S phase as determined by cell death as a result of treatment with tritiated thymidine, and surface antigenic features. Second, formation of in vitro colonies may prove a more sensitive indicator of occult metastatic disease than standard pathological studies. Third, such an assay could potentially be applied to develop individualized predictive trials of anti-cancer drugs in a manner analogous to techniques used for selection of antibacterial agents. Finally, full realization of the clinical application of bioassay of human tumor stem cell colonies with regard to their sensitivity to drugs, hormones, immunological agents, heat, and radiation could lead to major advances in clinical oncology.

It is thought that the invention and many of its attendant advantages will be understood from the foregoing description and it will be apparent that various changes may be made in the methods as described herein without departing from the spirit and scope of the invention or sacrificing its material advantages, the forms herein before described merely preferred embodiments thereof.

The embodiments of the invention in which an exclusive property or privilege is claimed are defined as follows:

1. An in vitro method for quantitatively assaying for the viable colony-forming tumor stem cell content of a sepcimen of primary explanted cells obtained from primary or metastatic human tumors employing a two-layer culture system exhibiting interlayer diffusibility of dissolved nutrients and growth factors, comprising the steps of:
   (a) forming a cell-free gelled underlayer comprising a liquid tissue culture feeder nutrient medium capable of supporting human tumor cell growth and a gelling agent for said feeder nutrient medium;
   (b) preparing a gelable liquid single-cell suspension of said explanted cells in a liquid tissue culture carrier nutrient medium capable of supporting human tumor cell growth and containing a gelling agent for said carrier nutrient medium;
   (c) plating said suspension onto said underlayer and allowing gelation thereof to occur, thereby forming a gelled overlayer which contains a known quantity of said explanted cells and which together with said underlayer constitutes said two-layer culture system, said culture system further containing a tumor stem cell colony growth-promoting concentration of METGF dissolved within at least one of said two layers, said METGF being a water-soluble tumor growth factor which is elaborated by macrophages;
   (d) incubating said culture system for a period of time sufficient to grow tumor stem cell colonies, the concentration of said explanted cells in said suspension being within a range enabling a substantially proportional relationship to exist between the total number of said explanted cells present in said overlayer and the total number of resulting tumor stem cell colonies grown during said incubation period; and
   (e) measuring the viable colony-forming tumor stem cell content of said overlayer as the total number of resulting tumor stem cell colonies grown during said incubation period.

2. The method of claim 1, wherein the concentration of METGF present in said culture system is within the range of from about 1.5 to about 15 units per milliliter of said culture system.

3. The method of claim 2, wherein the concentration of METGF present in said culture system is within the range of from about 6.25 to about 12.5 units per milliliter of said culture system.

4. The method of claim 1, wherein at least a portion of said METGF concentration present in said culture system originates from said underlayer.

5. The method of claim 4, wherein said feeder nutrient medium is a macrophage-conditioned nutrient medium containing METGF dissolved therein.

6. The method of claim 5, wherein said feeder nutrient medium is a nutrient medium which has been macrophage-conditioned by incubation with the adherent spleen cells of mineral oil-primed BALB/$_c$ mice and thereafter rendered cell-free.

7. The method of claim 5, wherein said feeder nutrient medium is a nutrient medium which has been macrophage-conditioned by incubation with the cells from a human B lymphocyte cell line and thereafter rendered cell-free.

8. The method of claim 1, wherein at least a portion of said METGF concentration present in said culture system originates from said overlayer.

9. The method of claim 8, wherein said explanted cells which are placed in said suspension include autologous macrophages, and the METGF originating from said overlayer is elaborated by said autologous macrophages.

10. The method of claim 1, wherein each of said gelling agents is agar.

11. The method of claim 1, wherein said incubation period ranges from about 7 days to about 21 days.

12. The method of claim 1, wherein said suspension contains a thiol in a concentration of from about $5\times10^{-5}$ M to about $5\times10^{-4}$ M.

13. The method of claim 12, wherein said thiol is selected from the group consisting of 2-mercaptoethanol and monothioglycerol.

14. The method of claim 1, wherein said incubation is carried out at a temperature of about 37° C. in a humidified atmosphere containing from about 5 to about 7.5 percent $CO_2$.

15. The method of claim 1, wherein prior to preparing said suspension, the explanted cells are subjected to a fractionation treatment so as to effect removal therefrom of contaminating non-tumor cells.

16. The method of claim 15, wherein said fractionation treatment comprises either velocity gradient sedimentation or adherent cell depletion or a combination thereof.

17. The method of claim 1, wherein the concentration of said explanted cells in said suspension is within the range of from about $1\times10^4$ to about $1\times10^6$ cells per milliliter.

18. An in vitro method for measuring drug sensitivity of the tumor stem cells of a specimen of primary explanted cells obtained from a primary or metastatic human tumor as an indication of the antineoplastic activity of a drug against said human tumor, said method comprising individually subjecting a test aliquot and a control aliquot of said specimen to an assay procedure for quantitatively determining the viable colony-forming tumor stem cell contents thereof, said test aliquot differing from said control aliquot in having been subjected to exposure with the drug to be tested, whereby the drug sensitivity at the drug exposure dose level tested may then be determined as the percent reduction in the assay count resulting from the drug exposure, said assay procedure employing a two-layer culture system exhibiting interlayer diffusibility of dissolved nutrients and growth factors and comprising the steps of:
   (a) forming a cell-free gelled underlayer comprising a liquid tissue culture feeder nutrient medium capable of supporting human tumor cell growth and a gelling agent for said feeder nutrient medium;
   (b) preparing a gelable liquid single-cell suspension of said explanted cells in a liquid tissue culture carrier nutrient medium capable of supporting human tumor cell growth and containing a gelling agent for said carrier nutrient medium;

(c) plating said suspension onto said underlayer and allowing gelation thereof to occur, thereby forming a gelled overlayer which contains a known quantity of said explanted cells and which together with said underlayer constitutes said two-layer culture system, said culture system further containing a tumor stem cell colony growth-promoting concentration of METGF dissolved within at least one of said two layers, said METGF being a water-soluble tumor growth factor which is elaborated by macrophages;

(d) incubating said culture system for a period of time sufficient to grow tumor stem cell colonies, the concentration of said explanted cells in said suspension being within a range enabling a substantially proportional relationship to exist between the total number of said explanted cells present in said overlayer and the total number of resulting tumor stem cell colonies grown during said incubation period; and (e) measuring the viable colony-forming tumor stem cell content of said overlayer as the total number of resulting tumor stem cell colonies grown during said incubation period.

19. The method of claim 18, wherein said drug exposure is carried out prior to step (b) of said assay procedure and comprises incubating said aliquot with a determinate concentration of said drug for a determinate period of time and thereafter separating said aliquot from said drug and washing said aliquot free of residual drug.

20. The method of claim 18, wherein said drug exposure is carried out by incorporating a determined concentration of said drug into said suspension in step (b) of said assay procedure and maintaining said drug in said overlayer throughout step (d) of said assay procedure for a determinate culture incubation period.

21. The method of claim 18, wherein said drug sensitivity measurements are carried out for a plurality of said drug exposure dose levels extending over a multi-log range, whereby the results of said drug sensitivity measurements may be integrated into a drug sensitivity index which is indicative of the antineoplastic activity of said drug against the specific human tumor from which said explanted cells were obtained.

22. The method of claim 21, wherein said drug sensitivity measurements are carried out for a plurality of different anticancer drugs which are potentially clinically effective for the chemotherapeutic treatment of the specific human tumor from which said explanted cells were obtained, whereby the relative drug sensitivity indices determined for each of the various drugs tested may be used for predictively selecting the most promisingly effective of said drugs to be used for said chemotherapeutic treatment.

23. The method of claim 21, wherein the maximum of said drug exposure dose levels is approximately 5 to 10 percent of the achievable peak dose level for said drug in vivo.

24. The method of claim 18, wherein said feeder nutrient medium employed in said assay procedure is a macrophage-conditioned nutrient medium containing METGF dissolved therein.

25. The method of claim 24, wherein said feeder nutrient medium is a nutrient medium which has been macrophage-conditioned by incubation with the adherent spleen cells of mineral oil-primed BALB/c mice and thereafter rendered cell-free.

* * * * *